United States Patent [19]

Moldenhauer et al.

[11] Patent Number: 5,985,296
[45] Date of Patent: Nov. 16, 1999

[54] COMPLEXES OF GAMMA-CYCLODEXTRIN AND RETINOL OR RETINOL DERIVATIVES, PROCESSES FOR THEIR PREPARATION AND THEIR USE

[75] Inventors: Jens-Peter Moldenhauer, Burghausen; Marlies Regiert, München; Thomas Wimmer, Marktl, all of Germany

[73] Assignee: Wacker-Chemie GmbH, München, Germany

[21] Appl. No.: 09/045,342

[22] Filed: Mar. 20, 1998

[30] Foreign Application Priority Data

Mar. 27, 1997 [DE] Germany .......................... 197 13 092

[51] Int. Cl.$^6$ .............................. A01N 43/04; A61K 6/00; A61K 7/00
[52] U.S. Cl. ............................................. 424/401; 514/58
[58] Field of Search .............................. 424/401; 514/58, 514/772, 844, 937

[56] References Cited

U.S. PATENT DOCUMENTS

| | | |
|---|---|---|
| 2,827,452 | 3/1958 | Schlenk et al. . |
| 4,371,673 | 2/1983 | Pitha ........................................ 525/426 |
| 5,024,998 | 6/1991 | Bodor . |
| 5,472,954 | 12/1995 | Loftsson ..................................... 514/58 |
| 5,484,816 | 1/1996 | Yanagida et al. ......................... 514/715 |
| 5,580,851 | 12/1996 | Trinh et al. ................................. 512/4 |
| 5,660,845 | 8/1997 | Trinh et al. ............................... 424/418 |

FOREIGN PATENT DOCUMENTS

| | | |
|---|---|---|
| 0335545 | 10/1989 | European Pat. Off. . |
| 0399716 | 11/1990 | European Pat. Off. . |
| 0579435 | 1/1994 | European Pat. Off. . |
| 0657176 | 6/1995 | European Pat. Off. . |
| 2108622 | 4/1990 | Japan . |
| 8200251 | 2/1982 | WIPO . |
| 9111172 | 8/1989 | WIPO . |
| 9014082 | 11/1990 | WIPO . |
| 9421225 | 9/1994 | WIPO . |

OTHER PUBLICATIONS

CA (Chemical Abstract) 98:52237 a "Vitamin–cyclodextrin compounds as food additives".

CA (Chemical Abstract) 110:199059u "Effect of β–cyclodextrin".

CA (Chemical Abstract) 120:265222b "Serum retinol analysis".

J. Drug Targeting 2(5) (1994), pp. 449–454 (CA 122:64224).

Derwent Publications, AN 90–167901, XP00270791& JP 02108622 A (Nisshin Flour Milling Co.)

Chemical Abstracts, vol. 126, No. 7, No. 98643, Munro Botella et al, XP002070790 & Analyst, Bd. 121, No. 11, 1996.

Primary Examiner—Thurman K. Page
Assistant Examiner—S. Howard
Attorney, Agent, or Firm—Collard & Roe, P.C.

[57] ABSTRACT

Complexes of γ-cyclodextrin and retinol or retinol derivatives, along with processes for their preparation and compositions for their use. The complexes are useful in cosmetic formulations and in pharmaceutical formulations.

12 Claims, No Drawings

COMPLEXES OF GAMMA-CYCLODEXTRIN AND RETINOL OR RETINOL DERIVATIVES, PROCESSES FOR THEIR PREPARATION AND THEIR USE

BACKGROUND OF THE INVENTION

1. Field of the Invention

The present invention relates to complexes of γ-cyclodextrin and retinol or retinol derivatives, to processes for their preparation and to their use.

2. The Prior Art

Cyclodextrins are cyclic oligosaccharides which are composed of 6, 7 or 8α(1–4)-linked anhydroglucose units. The α-, β- or γ-cyclodextrins prepared by the enzymatic conversion of starch differ in the diameter of their hydrophobic cavity and are generally suitable for inclusion of numerous lipophilic substances.

Retinol (vitamin A) is a fat-soluble vitamin composed of a cyclohexene ring with a side chain containing conjugated polyunsaturation. It is essential for humans inter alia and plays an important role particularly for vision. The daily requirement is met almost exclusively by the intake of β-carotene (provitamin A), which is converted into retinol enzymatically.

Because of its important physiological function, especially for vision, and also its skincare and antiwrinkle properties, retinol is an extremely valuable substance. In the cosmetics industry, there is great interest in the increased use of vitamin A, particularly in dermatological formulations.

Topical application of retinol stabilizes the vitamin A balance in the skin, which balance can be permanently impaired in particular by exposure to UV light. The deficiency of vitamin A leads to damage, particularly of the epidermis, and to increased formation of wrinkles and horn ("photoaging"). There is also a loss of the skin's elasticity. Moreover, the skin's barrier function against microorganisms is weakened.

The main problem that prevents the wide spread use of retinol is its sensitivity to oxidation, in particular oxidation caused by exposure to light. An autoxidation reaction takes place at the side chain of the molecule which contains the conjugated unsaturation. This reaction leads to the formation of numerous decomposition products, to isomerizations and to polymerizations. The originally crystalline retinol material becomes a viscous mass; and the pale yellow color of pure retinol becomes noticeably darker. As a result of peroxides which are formed as intermediates, the potentially toxic results of using these formulations increases. Also, the cosmetically desired results of the remaining intact retinol are reduced.

Instead of using the uncombined free retinol, which is very sensitive to oxidation, cosmetics, especially antiwrinkle creams, therefore often contain the less effective, but more stable retinyl ester. Examples of these more stable retinyl esters particularly include retinyl acetate and retinyl palmitate.

Moreover, retinol containing vitamin preparations are being marketed by the food industry. Furthermore, retinol can be used in pharmaceutical formulations.

Procedures which have the beneficial result of stabilizing pure retinol are thus of exceptional interest. Because free or uncombined retinol is extremely sensitive to oxidative decomposition, its use is severely limited, even though free retinol is highly desirable per se.

U.S. Pat. No. 2,827,452 discloses how retinol and also retinyl acetate and retinyl palmitate can be stabilized using β-cyclodextrin.

CA: 98:52237 describes the use of an α-cyclodextrin/retinol complex as an additive in food technology.

CA: 110:199059 describes how the photostability of retinyl acetate is increased by β-cyclodextrin and β-cyclodextrin derivatives in aqueous solution and in the solid state.

CA: 120:265222 discloses the complexation of retinyl acetate using β-cyclodextrin.

WO 94/21225 describes a skincare formulation comprising retinyl palmitate and β-cyclodextrin.

In WO 90/14082, retinoic acid is used together with β-cyclodextrin in an aqueous gel for dermatological purposes.

U.S. Pat. No. 5,484,816 discloses the stabilization of vitamin A and its corresponding fatty acid esters, which may also be present in dermatological formulations, by using antioxidants and UV-absorbers in the form of cyclodextrin complexes.

J. Drug Targeting 2(5) (1994) 449–54 (CA: 122:64224) reports on the complexation of retinol and retinoic acid using hydroxypropyl-β-cyclodextrin and on the inclusion of the corresponding complexes in liposomes.

U.S. Pat. No. 5,024,998 describes how, after parenteral application, the risk of undesired accumulation of retinol as a lipophilic pharmaceutical active substance can be lowered by solubilization using hydroxypropyl-β-cyclodextrin.

SUMMARY OF THE INVENTION

The present invention relates to compositions containing complexes of γ-cyclodextrin and retinol or retinol derivatives.

For the purposes of the invention, retinol derivatives are defined to mean retinyl esters (vitamin A esters) and vitamin A acid, (retinoic acid). Retinol derivatives are preferably defined to mean retinyl esters. In the following, the term complex includes retinol as well as retinol derivatives.

The complexes according to the invention have unexpectedly greater stability than known prior art cyclodextrin/retinol complexes.

Compared to the complexes of retinol with β-cyclodextrin, the complexes of the present invention achieve markedly improved stabilization of the active substance. The vitamin A content of the γ-cyclodextrin formulation of the invention following storage under atmospheric oxygen and irradiation with UVA light, was substantially greater than that of a corresponding β-cyclodextrin formulation. The complexes according to the invention thus make it possible for retinol and also retinol derivatives to be widely used in cosmetics, in pharmaceuticals, and in food products.

Despite the prior art possibility of using β-cyclodextrin or β-cyclodextrin derivatives for the inclusion and stabilization of retinol and retinol derivatives, extra stabilizer substances must necessarily be used with these β-cyclodextrin complexes. Thus, stabilizers preferentially have been added to these prior art formulations in order to increase the stabilization of retinol in the formulations.

This necessity for using extra stabilizers indicates that persons skilled in the art considered the possibility of increasing the stability of retinol using cyclodextrins or cyclodextrin derivatives to be nonexistant. Thus, these persons sought other ways for increasing the stability of retinol or its derivatives.

The novel complexes of γ-cyclodextrin with retinol of the present invention can be prepared by known processes. For example, they can be prepared from solution, or by using the paste kneading procedure. The present invention thus further relates to processes which comprise complexing retinol or complexing a retinol derivative using γ-cyclodextrin.

Surprisingly, it has been found that retinol can be complexed and stabilized in an excellent manner by γ-cyclodextrin. The processes according to the present invention stabilize retinol and protect retinol from oxidative decomposition to a greater extent than the known prior art processes.

The preparation of the complexes according to the invention from concentrated, aqueous γ-cyclodextrin solutions has been found to be advantageous. The γ-cyclodextrin concentration in the aqueous solution ranges from 5% to 50% by weight, based upon the total solution weight. Preferably the γ-cyclodextrin concentration in the aqueous solution ranges from 20% to 50% by weight, based upon the total solution weight. The weight ratio of retinol to γ-cyclodextrin ranges between 1:20 and 1:1, and preferably ranges between 1:12 and 1:4.

The formulations are thoroughly mixed, for example, by vigorously stirring or kneading, depending on the consistency of the formulation.

The reaction temperature preferably ranges from 20° C.–80° C., particularly preferably ranges from 20° C.–60° C., and especially preferably ranges from 40° C.–60° C. The reaction time depends upon the temperature and is between one hour and several days. A reaction time of from 12 to 96 hours is preferred. The complexation reaction is preferably carried out under atmospheric pressure. The complexation reaction is preferably carried out under a protective gas atmosphere such as nitrogen or argon.

The complexes, which are sparingly soluble in water, can be used directly in the form of the reaction product mixture. They can, however, also be isolated and treated by filtration, centrifugation, drying, grinding, sieving, screening, granulation or tableting by the customary methods in each case.

Depending upon the application, for example, in cosmetic formulations, other suitable substances or additives can also be added to the γ-cyclodextrin complexes. These other suitable substances include inert, non-toxic topically acceptable carrier materials. Thus, it is possible to add, for example, humectants, surfactants, detergent additives, skincare additives, self-tanning additives, thickeners, preservatives, stabilizers, emulsifiers, perfumes, dyes, antioxidants, vitamins, UV filters and silicone oils.

Inert means that the carrier does not react with the γ-cyclodextrin complex. Non-toxic means that the carrier is not harmful when applied topically.

Thus, the invention further relates to cosmetic composition formulations which comprise a cosmetically effective amount of the complex. This effective amount ranges from 0.1% to 5% by weight, and preferably from 0.4% to 1% by weight based upon the total cosmetic composition formulation weight, of the γ-cyclodextrin/retinol complex or the γ-cyclodextrin/retinol derivative complex. The balance of the formulation up to 100% by weight is the above-mentioned additives which are customary for cosmetic formulations. Thus, the amount of these additives ranges from 95% to 99.9% by weight, and preferably from 99% to 99.6% by weight, based upon the total cosmetic composition formulation weight.

The invention further relates to pharmaceutical composition formulations which comprise a pharmaceutically effective amount of the complex. This effective amount ranges from 0.1% to 5% by weight and preferably from 0.4% to 1% by weight based upon the total pharmaceutical composition formulation weight, of the γ-cyclodextrin/retinol complex or the γ-cyclodextrin/retinol derivative complex. The balance of the formulation up to 100% by weight is additives customary for pharmaceutical formulations. The customary additives suitable for pharmaceutical formulations are those ingredients which are inert, non-toxic and pharmaceutically acceptable. Examples include thickeners, preservatives, stabilizers, emulsifiers, antioxidants and vitamins. The amount of these additives ranges from 95% to 99.9% by weight, and preferably from 99% to 99.6% by weight based upon the total pharmaceutical composition formulation weight.

Examples of other suitable substances include the following. Particularly preferred surfactants include nonionics such as polyethylene glycols, polypropylene glycols and mixtures thereof.

Particularly preferred as a detergent additive is sodium lauryl sulfate. Particularly preferred skincare additives include anti-acne agents such as benzoyl peroxide and resorcinol. Particularly preferred self-tanning additives include tannic acid and aluminum tannate. Particularly preferred thickeners include waxes, polyethylene glycol stearate, glyceryl stearate, kaolin, and almond bran. Particularly preferred preservatives include methylparaben and propylparaben. Particularly preferred stabilizers include sodium hydroxide and potassium hydroxide. Particularly preferred emulsifiers include polysorbates, stearic acid, cetyl alcohol, macadamia nut oil, jojoba oil and avocado oil. Particularly preferred as a dye additive is the hair dying agent hydrogen peroxide.

Particularly preferred antioxidants include zinc and selenium. Particularly preferred vitamins include vitamin B, vitamin C, and vitamin E. Particularly preferred UV filters include sunscreen agents such as octyl methoxycinnimate and butyl methoxydibenzoyl methane. Particularly preferred humectants include glycerin, isopropyl myristate, glycerin monomyristate, and isopropyl palmitate.

Both the cosmetic composition formulations and the pharmaceutical composition formulations are safe and effective.

DETAILED DESCRIPTION OF PREFERRED EMBODIMENTS

Other objects and features of the present invention will become apparent from the following Examples, which disclose the embodiments of the present invention. It should be understood, however, that the Examples are designed for the purpose of illustration only and not as a definition of the limits of the invention.

EXAMPLE 1

Complexation of retinol with β-cyclodextrin and γ-cyclodextrin for a comparison of the storage stability a) (Comparative Example) 78.5 g of β-cyclodextrin were dissolved in 1520 ml of boiled and nitrogen-saturated distilled water at 55° C., and 10 g of retinol were added under a nitrogen protective gas atmosphere. The formulation was stirred at this temperature for 72 h. After the mixture had been cooled to room temperature, the complex was isolated by filtration and dried under reduced pressure. The yield was 79.2 g.

b) (Example according to the invention) 1097 g of γ-cyclodextrin were mixed with 1900 ml of distilled water in a thermostated vessel with ground glass joints. The mixture was heated to 90° C. and cooled to 50° C. under nitrogen. After 100 g of retinol had been added, the formulation was stirred vigorously at 50° C. for 72 h and then cooled to room temperature. The resulting complex was filtered off with vacuum suction and was dried under reduced pressure. Yield: 1125 g.

EXAMPLE 2

Preparation of a retinol/γ-cyclodextrin complex by the kneading method 370 g of γ-cyclodextrin were mixed with 280 ml of boiled and nitrogen-saturated distilled water in a kneading machine to give a paste. 40 g of retinol were then added under a nitrogen protective gas atmosphere. The mixture was heated to 50° C. and stirred or kneaded at this temperature for 6 h with the addition of more water. After the mixture had cooled to room temperature, the product was removed and the complex was obtained by drying under reduced pressure.

EXAMPLE 3

Comparative tests to determine the storage stability of retinol as β-cyclodextrin and γ-cyclodextrin complex 50 g of each of the complexes of retinol with β-cyclodextrin and γ-cyclodextrin (as in Example 1a–b) were poured into flat Petri dishes and irradiated at room temperature with UVA light having a wavelength of 366 nm. The samples were homogenized by stirring prior to content determination. Table 1 lists the retinol contents determined by HPLC analysis. The stabilizing effect is clearly more pronounced in the case of the γ-cyclodextrin complex than in the case of the β-cyclodextrin complex.

TABLE 1

| Storage time | Retinol content | | | |
|---|---|---|---|---|
| | Retinol/β-CD complex | | Retinol/γ-CD complex | |
| [days] | absolute | relative | absolute | relative |
| 0 | 7.1% | 100% | 8.9% | 100% |
| 4 | 1.7% | 23.9% | 5.0% | 56.2% |
| 7 | 1.0% | 14.1% | 3.6% | 40.5% |
| 48 | 0.0% | 0.0% | 1.6% | 18.0% |

EXAMPLE 4

Comparison of a γ-cyclodextrin complex with a lactose trituration of retinol

4a: 45 g of γ-cyclodextrin were dissolved at 50° C. in 100 ml of distilled water. After 5 g of retinol had been added, the reaction mixture was stirred for 48 h under a nitrogen protective gas atmosphere and the precipitated complex was isolated by filtration and dried under reduced pressure. Yield: 47 g with a vitamin content of 10%.

4a: 45 g of β-D-lactose were vigorously triturated with 5 g of retinol in a mortar, until a homogeneous powder having a vitamin content of 10% was obtained.

40 g of each of the γ-cyclodextrin complex (4a) and the lactose trituration (4b) were stored in open Petri dishes at room temperature and in daylight. Samples of the substances 4a and 4b were taken at intervals of 4, 7, 21 and 48 days from the start of storage and the content of still intact retinol was determined by HPLC analysis. Table 2 shows the results obtained.

TABLE 2

| Storage time | Retinol content | | | |
|---|---|---|---|---|
| | Retinol/lactose trituration | | Retinol/γ-CD complex | |
| [days] | absolute | relative | absolute | relative |
| 0 | 8.8% | 100% | 8.9% | 100% |
| 4 | 5.4% | 61.4% | 8.2% | 92.1% |
| 7 | 3.5% | 39.8% | 7.8% | 87.6% |
| 21 | 1.4% | 15.9% | 6.4% | 71.9% |
| 48 | 0.2% | 2.3% | 5.6% | 62.9% |

EXAMPLE 5

Preparation of a retinyl acetate/γ-cyclodextrin complex by the kneading method 250 g of γ-cyclodextrin were mixed with 160 ml of boiled and nitrogen-saturated distilled water in a kneading machine to give a paste. 63 g of retinyl acetate were then mixed in under a nitrogen protective gas atmosphere. The paste was heated to 55° C. and kneaded at this temperature for 8 h with the addition of more water. After the mixture had cooled to room temperature, the product was removed and the complex obtained by drying under reduced pressure.

EXAMPLE 6

Face pack in powder form (for self-preparation)

| Composition: | Parts by Weight: |
|---|---|
| 1) Kaolin | 300 |
| 2) Almond bran (sieved) | 145 |
| 3) γ-Cyclodextrin complex with 25% by weight of evening primrose oil | 550 |
| 4) γ-Cyclodextrin complex with 9.8% by weight retinol | 5 |
| TOTAL | 1000 |

Preparation of the powder formulation

Constituents 1–4 were formulated into a powder by a combined mixing, grinding and sieving process steps.

Preparation of the face pack 2 tablespoons of the powder were mixed with warm water to give a paste and applied to the skin sufficiently thickly but such that it could still be spread. After 15 minutes it was washed off with warm water.

EXAMPLE 7

Body emulsion

| Composition: | Parts by Weight: |
|---|---|
| 1) Glycerin monomyristate | 14 |
| 2) Stearic acid | 12 |
| 3) Cetyl alcohol | 5 |

-continued

| Composition: | Parts by Weight: |
|---|---|
| 4) Isopropyl polmitate | 50 |
| 5) γ-Cyclodextrin complex with 9.8% by weight retinol | 4 |
| 6) Distilled water | 905 |
| 7) Methylparaben | 10 |
| TOTAL: | 1000 |

Preparation

Starting materials 1–5 were introduced into a beaker, and starting materials 6 and 7 were mixed in a stirred vessel and heated to 65° C. The two mixtures were then emulsified at 65° C. using a high-speed paddle stirrer. With further stirring, the mixture was cooled to 40° C. and homogenized using an Ultra-Turrax (max. 500 rpm). The air dissolved in the cream was removed by carefully applying a water-pump vacuum.

EXAMPLE 8

Antiwrinkle cream

| Composition: | Parts by Weight: |
|---|---|
| 1) Distilled water | 650 |
| 2) γ-Cyclodextrin | 100 |
| 3) Macadamia nut oil | 190 |
| 4) Jojoba oil | 30 |
| 5) Avocado oil | 20 |
| 6) γ-Cyclodextrin complex with 9.8% by weight retinol | 10 |
| TOTAL: | 1000 |

Preparation

Starting materials 1 and 2 were introduced into a beaker and heated to 50° C. The macadamia nut oil was added and the mixture was homogenized for 2 hours with a stirrer at high speed. With further stirring, the mixture was cooled. Starting materials 4–6 were added; and the mixture was homogenized for a further 10 minutes using an Ultra-Turrax (max. 500 rpm).

The optimum viscosity of the cream was reached after a storage time of 5 days.

While several embodiments of the present invention have been shown and described, it is to be understood that many changes and modifications may be made thereunto without departing from the spirit and scope of the invention as defined in the appended claims.

What is claimed is:

1. A composition consisting of a complex selected from the group consisting of γ-cyclodextrin with retinol, and γ-cyclodextrin with a retinol derivative selected from the group consisting of retinyl esters and retinoic acid;

wherein said retinol and retinol derivative and said γ-cyclodextrin are present in a weight ratio of retinol to γ-cyclodextrin ranging between 1:20 and 1:1.

2. A process for stabilizing retinol or a retinol derivative in a γ-cyclodextrin complex, which consists of reacting γ-cyclodextrin with a substance selected from the group consisting of retinol and a retinol derivative selected from the group consisting of retinyl esters and retinoic acid in a complexing reaction to produce a complex of γ-cyclodextrin and said substance;

wherein said substance and said γ-cyclodextrin are present in a weight ratio of substance to γ-cyclodextrin ranging between 1:20 and 1:1.

3. The process as claimed in claim 2, which comprises carrying out the complexing reaction in an aqueous γ-cyclodextrin solution having a γ-cyclodextrin concentration ranging from 5% to 50% by weight based upon the total solution weight.

4. The process as claimed in claim 2, which comprises carrying out the complexing reaction by kneading an aqueous γ-cyclodextrin paste having a γ-cyclodextrin concentration ranging from 25% to 80% by weight based upon the total paste weight.

5. The process as claimed in claim 2, wherein said retinol and said γ-cyclodextrin are present in a weight ratio of retinol to γ-cyclodextrin ranging between 1:12 and 1:4.

6. The process as claimed in claim 2, wherein the complexing reaction is carried out at a temperature ranging from 20° C. to 80° C.

7. The process as claimed in claim 2, which comprises carrying out the complexing reaction under a protective gas atmosphere.

8. A cosmetic formulation composition consisting of a cosmetically effective amount of a complex selected from the group consisting of γ-cyclodextrin with retinol and γ-cyclodextrin with a retinol derivative selected from the group consisting of retinyl esters and retinoic acid;

wherein said retinol and retinol derivative and said γ-cyclodextrin are present in a weight ratio of retinol to γ-cyclodextrin ranging between 1:20 and 1:1; and an inert non-toxic topically acceptable carrier for the cosmetic formulation.

9. A pharmaceutical formulation composition consisting of a pharmaceutically effective amount of a complex selected from the group consisting of γ-cyclodextrin with retinol and γ-cyclodextrin with a retinol derivative selected from the group consisting of retinyl esters and retinoic acid;

wherein said retinol and retinol derivative and said γ-cyclodextrin are present in a weight ratio of retinol to γ-cyclodextrin ranging between 1:20 and 1:1; and an inert non-toxic pharmaceutically acceptable carrier for the pharmaceutical formulation.

10. A face pack composition in powder form consisting of

| | Parts by Weight: |
|---|---|
| 1) Kaolin | 300 |
| 2) Almond bran (sieved) | 145 |
| 3) γ-Cyclodextrin complex with 25% by weight of evening primrose oil | 550 |
| 4) γ-Cyclodextrin complex with 9.8% by weight retinol | 5 |
| TOTAL | 1000 |

11. A body emulsion composition consisting of

|  | Parts by Weight: |
|---|---|
| 1) Glycerin monomyristate | 14 |
| 2) Stearic acid | 12 |
| 3) Cetyl alcohol | 5 |
| 4) Isopropyl palmitate | 50 |
| 5) γ-Cyclodextrin complex with 9.8% by weight retinol | 4 |
| 6) Distilled water | 905 |
| 7) Methylparaben | 10 |
| TOTAL | 1000 |

12. An anti-wrinkle cream composition consisting of

|  | Parts by Weight: |
|---|---|
| 1) Distilled water | 650 |
| 2) γ-Cyclodextrin | 100 |
| 3) Macadamia nut oil | 190 |
| 4) Jojoba oil | 30 |
| 5) Avocado oil | 20 |
| 6) γ-Cyclodextrin complex with 9.8% by weight retinol | 10 |
| TOTAL | 1000 |

* * * * *